(12) United States Patent
Rogers et al.

(10) Patent No.: US 8,309,760 B2
(45) Date of Patent: Nov. 13, 2012

(54) PROCESS FOR PURIFICATION OF ARYL CARBOXYLIC ACIDS

(75) Inventors: Robin D. Rogers, Tuscaloosa, AL (US); Allan S. Myerson, Chicago, IL (US); Christopher Corey Hines, Colfax, WA (US)

(73) Assignee: University of Alabama, Tuscaloosa, AL (US)

( * ) Notice: Subject to any disclaimer, the term of this patent is extended or adjusted under 35 U.S.C. 154(b) by 335 days.

(21) Appl. No.: 12/601,668

(22) PCT Filed: May 30, 2008

(86) PCT No.: PCT/US2008/065348
§ 371 (c)(1),
(2), (4) Date: Nov. 24, 2009

(87) PCT Pub. No.: WO2008/151034
PCT Pub. Date: Dec. 11, 2008

(65) Prior Publication Data
US 2010/0174111 A1   Jul. 8, 2010

Related U.S. Application Data

(60) Provisional application No. 60/932,511, filed on May 31, 2007.

(51) Int. Cl.
*C07C 51/42* (2006.01)

(52) U.S. Cl. ...................................................... 562/486

(58) Field of Classification Search ........................ None
See application file for complete search history.

(56) References Cited

U.S. PATENT DOCUMENTS

| 4,702,857 A | 10/1987 | Gosselink |
| 6,320,083 B1 | 11/2001 | Saleh |
| 7,094,925 B2 * | 8/2006 | Earle et al. .................... 562/410 |
| 2005/0164963 A1 | 7/2005 | Essler et al. |

OTHER PUBLICATIONS

Armstrong, D. W. et al., Structure and properties of high stability geminal dicationic ionic liquids, J. Amer. Chem. Soc. 2005;127(2):593-604.
Kirschner M., PTA/DMT, Chemical Market Reporter Nov. 22-29, 2004;266(18):31.
Kleerebezem R et al., High rate treatment of terephthalic acid production wastewater in a two-stage anaerobic bioreactor, Biotechnol. Bioeng. Jul. 20, 2005;91(2):169-79.
Rogers, R. D., et al., 1,3-Dimethylimidazolium-2-carboxylate: the unexpected synthesis of an ionic liquid precursor and carbene-CO2 adduct, Chem. Commun.; 2003: 28-29.
Rogers, R. D. et al., Mercury(II) partitioning from aqueous solutions with a new, hydrophobic ethylene-glycol functionalized bisimidazolium ionic liquid, Green Chem. 2003;5:129-135.
Thiruvenkatachari R. et al., Degradation of Phthalic Acids and Benzoic Acid from Terephthalic Acid Wastewater by Advanced Oxidation Processes, J. Enviro. Sci. and Health Part A: Toxic/Hazardous Substances & Environmental Engineering, 2006; 41(8), 1685-1697.
Wang et al., "solubilities of 4-carboxybenzaldehyde and 1,4-benzenedicarboxylic acid in N-methyl-2-pyrrolidone in the temperature range from 343.2 to 468.2 K" J. Chem. Eng. Data 2005, 50:243-245.

* cited by examiner

*Primary Examiner* — Yevegeny Valenrod
(74) *Attorney, Agent, or Firm* — McKeon, Meunier, Carlin & Curfman, LLC (57) ABSTRACT

Disclosed herein is a process for purifying aryl carboxylic acids, in particular terephthalic acid, wherein the impure acid is dissolved or dispersed in an ionic liquid and a non-solvent is added to precipitate the purified acid. The present disclosure further relates to compositions comprising terephthalic acid and one or more ionic liquids.

6 Claims, 5 Drawing Sheets

PXRD spectra of crystalline terephthalic acid obtained from compositions comprising various ionic liquids.

Figure 1

CALIBRATION CURVE:

—●— terephthalic acid

—▲— 4-carboxybenzaldehyde

Linearity is maintained in the range of 0.1 ppm to 20 ppm for each solute.

Figure 2

[1,3-dimethylimidazolium][terephthalic acid]

Figure 3

[1,3-dimethylimidazolium]$_2$[terephthalic acid]

PROCESS FOR PURIFICATION OF ARYL CARBOXYLIC ACIDS

CROSS-REFERENCE TO RELATED APPLICATIONS

This application claims the benefit of U.S. Provisional Application Ser. No. 60/932,511, filed on May 31, 2007, which is incorporated herein by reference in its entirety.

FIELD OF THE DISCLOSURE

The present disclosure relates to a low cost method for purifying aryl carboxylic acids, to compositions comprising terephthalic acid and one or more ionic liquids, to compositions useful for reacting aryl carboxylic acids with one or more reagents, and to salts comprising an aryl carboxylic acid anion.

BACKGROUND

Terephthalic acid is one of the largest commodity chemicals manufactured worldwide with production estimated at 8.49 billion pounds yearly (See Kirschner M., PTA/DMT, *Chemical Market Reporter* 2004 Nov. 22-29; 266(18):31). Terephthalic acid is used as a starting material monomer in the production of a wide range of polyethylene terephthalates, from soil release polymers for use in laundry detergents (U.S. Pat. No. 4,702,857) to the manufacture of plastic bottles and containers.

Terephthalic acid is typically manufactured by the air oxidation of 1,4-dimethyl-benzene (para-xylene) in acetic acid employing a cobalt molybdenum catalyst. Because the reaction does not result in 100% conversion, impurities are usually present, most notably 4-carboxybenzaldehyde (4-CBA). However, in order to use terephthalic acid as a starting material, for example, for the preparation of polyethylene terephthalate copolymers, terephthalic acid must be very pure.

One commercial process for the purification of terephthalic acid involves dissolving the impure terephthalic acid in water at a temperature of about 300° C. where the solubility of terephthalic acid is about 40%. At this point, most of the 4-CBA is removed and the terephthalic acid is crystallized through a series of 5-6 crystallizers, which operate at sequentially lower temperatures and pressures.

In order to purify the crude terephthalic acid by such methods, large quantities of energy and water are necessary. Indeed, recovery of the large quantities of water that are rendered unusable during the purification of terephthalic acid has itself been the subject of much research. (See Kleerebezem R et al., High rate treatment of terephthalic acid production wastewater in a two-stage anaerobic bioreactor, *Biotechnol. Bioeng.* 2005 Jul. 20; 91(2):169-79; and Thiruvenkatachari R. et al., Degradation of Phthalic Acids and Benzoic Acid from Terephthalic Acid Wastewater by Advanced Oxidation Processes, *J. Enviro. Sci. and Health* Part A: Toxic/Hazardous Substances & Environmental Engineering, 2006; 41(8), 1685-1697.)

There is, therefore, a long felt need for a low temperature and low water volume process for purifying terephthalic acid. The compositions, methods and devices disclosed herein meet these and other needs.

SUMMARY

The present disclosure meets the aforementioned needs in that disclosed herein are compositions comprising an aryl carboxylic acid and an ionic liquid, processes for purifying aryl carboxylic acids, inter alia, terephthalic acid and naphthalene dicarboxylic acid, processes for modifying aryl carboxylic acids or compositions useful for reacting aryl carboxylic acids with one or more reagents, and to salts comprising an aryl carboxylic acid anion.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION

In this specification and in the claims that follow, reference will be made to a number of terms, which shall be defined to have the following meanings:

Substituted and unsubstituted acyclic units comprising from 1 to 24 carbon atoms encompass 3 categories of units: linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like; linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like; and linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-

5-methylhex-3-ynyl ($C_7$), 6-hydroxy-6-methylhept-3-yn-2-yl ($C_8$), 5-hydroxy-5-ethylhept-3-ynyl ($C_9$), and the like.

Substituted and unsubstituted cyclic units comprising from 3 to 24 carbon atoms encompass the following units: carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), decalinyl ($C_{10}$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$); carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$); and carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Substituted and unsubstituted aryl units comprising from 6 to 24 carbon atoms encompass the following units: $C_6$, $C_{10}$, or $C_{14}$ substituted or unsubstituted aryl rings; phenyl, naphthyl, anthracenyl, phenanthryl, and the like whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tent-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyanonaphthylen-1-yl ($C_{10}$); $C_6$, $C_{10}$, or $C_{14}$ aryl rings fused with 1 or 2 saturated rings non-limiting examples of which include, bicyclo[4.2.0]octa-1,3,5-trienyl ($C_8$), and indanyl ($C_9$).

Substituted and unsubstituted heterocyclic or heteroaryl units comprising from 1 to 24 carbon atoms encompasses the following units all of which contain at least one heteroatom in at least one ring chosen from nitrogen (N), oxygen (O), sulfur (S), phosphorous (P) or mixtures of N, O, S, and P: heterocyclic units having a single ring containing one or more heteroatoms chosen from nitrogen (N), oxygen (O), or sulfur (S), or mixtures of N, O, and S, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$); heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$); heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$); heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-c]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

The term "arylalkylene" is used throughout the specification to refer to substituted or unsubstituted $C_6$, $C_{10}$, or $C_{14}$ aryl rings tethered to another unit through a substituted or unsubstituted $C_1$-$C_{12}$ alkylene unit. These units can be referred to by indicating the number of carbons contained in the alkylene unit followed by the number of carbon atoms in the aryl unit, or by their chemical name. A non-limiting example of tethered cyclic hydrocarbyl units includes a substituted or unsubstituted benzyl. A substituted or unsubstituted benzyl unit contains a tether containing one carbon atom (methylene) and a substituted or unsubstituted aryl ring containing six carbon atoms, or a $C_1$-($C_6$) unit, having the formula:

wherein $R^a$ is optionally one or more independently chosen substitutions for hydrogen. Further examples include other aryl units, inter alia, (2-hydroxyphenyl)hexyl $C_6$-($C_6$); naphthalen-2-ylmethyl $C_1$-($C_{10}$), 4-fluorobenzyl $C_1$-($C_6$), 2-(3-hydroxy-phenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$).

The terms "heteroarylalkylene" and "heterocyclicalkylene" are used throughout the specification to refer to substituted or unsubstituted heteroaryl and heterocyclic rings as defined herein above containing from 1 to 24 carbon atoms that are tethered to another unit through a substituted or unsubstituted $C_1$-$C_{12}$ alkylene unit. These units can be referred to by indicating the number of carbons contained in the alkylene unit followed by the number of carbon atoms in the heteroaryl and heterocyclic unit, or by their chemical name. A non-limiting example includes substituted and unsubstituted $C_1$-$C_{10}$ alkylene-heteroaryl units, for example a 2-picolyl $C_1$-($C_6$) unit having the formula:

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. A three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a "substituted $C_8$ linear alkyl unit", 3-guanidinopropyl is a "substituted $C_3$ linear alkyl unit," and 2-carboxypyridinyl is a "substituted heteroaryl unit."

The following are non-limiting examples of units which can substitute for hydrogen atoms on a carbocyclic, aryl, heterocyclic, or heteroaryl unit:
 i) $C_1$-$C_4$ linear or branched alkyl; for example, methyl ($C_1$), ethyl ($C_2$), n-propyl ($C_3$), iso-propyl ($C_3$), n-butyl ($C_4$), iso-butyl ($C_4$), sec-butyl ($C_4$), and tert-butyl ($C_4$);
 ii) —$OR^{12}$; for example, —OH, —$OCH_3$, —$OCH_2CH_3$, —$OCH_2CH_2CH_3$;
 iii) —$C(O)R^{12}$; for example, —$COCH_3$, —$COCH_2CH_3$, —$COCH_2CH_2CH_3$;
 iv) —$C(O)OR^{12}$; for example, —$CO_2CH_3$, —$CO_2CH_2CH_3$, —$CO_2CH_2CH_2CH_3$;
 v) —$C(O)N(R^{12})_2$; for example, —$CONH_2$, —$CONHCH_3$, —$CON(CH_3)_2$;
 vi) —$N(R^{12})_2$; for example, —$NH_2$, —$NHCH_3$, —$N(CH_3)_2$, —$NH(CH_2CH_3)$;
 vii) halogen: —F, —Cl, —Br, and —I;
 viii) —$CH_mX_n$; wherein X is halogen, m is from 0 to 2, m+n=3; for example, —$CH_2F$, —$CHF_2$, —$CF_3$, —$CCl_3$, or —$CBr_3$; and
 ix) —$SO_2R^{12}$; for example, —$SO_2H$; —$SO_2CH_3$; —$SO_2C_6H_5$ wherein each $R^{12}$ is independently hydrogen, substituted or unsubstituted $C_1$-$C_4$ linear, branched, or cyclic alkyl; or two $R^{12}$ units can be taken together to form a ring comprising 3-7 atoms. Substituents suitable for replacement of a hydrogen atom are further defined herein below.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an ionic liquid" includes mixtures of two or more such ionic liquids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Compositions

The present disclosure relates to compositions comprising one or more aryl carboxylic acid and one or more ionic liquids. Examples of aryl carboxylic acids include aryl monocarboxylic acids, inter alia, naphthalene carboxylic acid, and aryl dicarboxylic acids, inter alia, terephthalic acid and naphthylene dicarboxylic acid. Non-limiting examples of aryl carboxylic acids include, but are not limited to, benzoic acid, phthalic acid, isophthalic acid, terephthalic acid, naphthalene-1,2-dicarboxylic acid, naphthalene-1,3-dicarboxylic acid, naphthalene-1,4-dicarboxylic acid, naphthalene-1,5-dicarboxylic acid, naphthalene-1,6-dicarboxylic acid, naphthalene-1,7-dicarboxylic acid, naphthalene-1,8-dicarboxylic acid, naphthalene-2,3-dicarboxylic acid, naphthalene-2,6-dicarboxylic acid, naphthalene-2,7-dicarboxylic acid, 1,3,5-tricarboxylic benzoic acid, naphthalene-1,2,3-tricarboxylic acid, naphthalene-1,2,4-tricarboxylic acid, naphthalene-1,2,5-tricarboxylic acid, naphthalene-1,2,6-tricarboxylic acid, naphthalene-1,2,7-tricarboxylic acid, naphthalene-1,2,8-tricarboxylic acid, naphthalene-1,3,5-tricarboxylic acid, naphthalene-1,3,6-tricarboxylic acid, naphthalene-1,3,7-tricarboxylic acid, naphthalene-1,3,8-tricarboxylic acid, naphthalene-1,4,6-tricarboxylic acid, naphthalene-2,3,5-tricarboxylic acid, and naphthalene-2,3,6-tricarboxylic acid, and the like. A non-limiting example of a substituted aryl carboxylic acid includes 5-sulfo-isophthalic acid.

The disclosed compositions can comprise from about 0.001% to about 99.9% by weight of one or more aryl carboxylic acids. In one embodiment the compositions can comprise from about 0.1% to about 50% by weight of one or more aryl carboxylic acids. In another embodiment the compositions can comprise from about 0.1% to about 25% by weight of one or more aryl carboxylic acids. In yet another embodiment the compositions can comprise from about 5% to about 20% by weight of one or more aryl carboxylic acids. In a still further embodiment the compositions can comprise from about 50% to about 99% by weight of one or more aryl carboxylic acids. In a yet further embodiment the compositions can comprise from about 0.1% to about 10% by weight of one or more aryl carboxylic acids. In a yet still further embodiment the compositions can comprise from about 10% to about 25% by weight of one or more aryl carboxylic acids.

The disclosed compositions can comprise from about 0.1% to about 99.999% by weight of one or more ionic liquids. In one embodiment the compositions can comprise from about 50% to about 99.9% by weight of one or more ionic liquids. In another embodiment the compositions can comprise from about 75% to about 99.9% by weight of one or more ionic liquids. In yet another embodiment the compositions can comprise from about 80% to about 95% by weight of one or more ionic liquids. In a still further embodiment the compositions can comprise from about 1% to about 50% by weight of one or more ionic liquids. In a yet further embodiment the compositions can comprise from about 90% to about 99.9% by weight of one or more ionic liquids. In a yet still further embodiment the compositions can comprise from about 75% to about 90% by weight of one or more ionic liquids.

The following are non-limiting examples of compositions according to the present disclosure. An embodiment of the compositions disclosed herein can comprise from about 0.001% to about 99.9% by weight of terephthalic acid; and from about 0.1% to about 99.999% by weight of one or more ionic liquids. Another embodiment of the compositions disclosed herein can comprise from about 0.1% to about 50% by weight of terephthalic acid; and from about 50% to about 99.9% by weight of one or more ionic liquids. A yet another embodiment of the compositions disclosed herein can comprise from about 0.1% to about 25% by weight of terephthalic acid; and from about 75% to about 99.9% by weight of one or more ionic liquids. A further embodiment of the compositions disclosed herein can comprise from about 5% to about 20% by weight of terephthalic acid; and from about 80% to about 95% by weight of one or more ionic liquids. An another further embodiment of the compositions disclosed herein can comprise from about 50% to about 99% by weight of terephthalic acid; and from about 1% to about 50% by weight of one or more ionic liquids.

A yet another further embodiment of the compositions disclosed herein can comprise from about 0.1% to about 10% by weight of terephthalic acid; and from about 90% to about 99.9% by weight of one or more ionic liquids. A yet still further embodiment of the compositions disclosed herein can comprise from about 10% to about 25% by weight of terephthalic acid; and from about 75% to about 90% by weight of one or more ionic liquids.

The compositions disclosed herein can further comprise one or more impurities.

The following are embodiments that describe the amount of impurity present in the aryl carboxylic acid. One embodiment of the disclosed compositions can comprise one or more aryl carboxylic acids that can comprise from about 0.01% to about 20% by weight of one or more impurities. Another embodiment of the disclosed compositions can comprise one or more aryl carboxylic acids that can comprise from about 0.01% to about 10% by weight of one or more impurities. A further embodiment of the disclosed compositions can comprise one or more aryl carboxylic acids that can comprise from about 1% to about 5% by weight of one or more impurities. A yet another embodiment of the disclosed compositions can comprise one or more aryl carboxylic acids that can comprise from about 4% to about 10% by weight of one or more impurities. A yet further embodiment of the disclosed compositions can comprise one or more aryl carboxylic acids that can comprise from about 0.5% to about 7% by weight of one or more impurities. In still a further embodiment of the disclosed compositions can comprise one or more aryl carboxylic acids that can comprise from about 0.1% to about 0.5% by weight of one or more impurities. However, the amount of the one or more impurities present can be present in the aryl carboxylic acid in any whole number amount or fractional part thereof within the above described embodiments, for example, 1.2%, 1.5%, 2%, 3.33%, 4.105%, and the like.

A non-limiting example of a composition according to the present disclosure comprises:
a) from about 5% to about 20% by weight of terephthalic acid;
b) from about 0.1% to about 0.5% by weight of one or more impurities; and
c) the balance one or more ionic liquids.

A further non-limiting example of a composition according to the present disclosure comprises:
a) from about 5% to about 20% by weight of impure terephthalic acid, impure terephthalic acid comprising:
 i) from about 95% to about 99% by weight of terephthalic acid;
 ii) from about 1% to about 5% by weight of one or more impurities; and
b) from about 80% to about 95% by weight of one or more ionic liquids.

One particular impurity that comprises the compositions disclosed herein is 4-carboxybenzaldehyde (4-CBA). Typically this impurity is present in compositions comprising freshly manufactured terephthalic acid. 4-CBA can be present in an amount of from about 0.001% to about 20% by weight of terephthalic acid. Alternatively, CBA can comprise of from about 0.01% to about 10% by weight of a composition comprising terephthalic acid and one or more ionic liquids. In addition, 4-CBA can be present in any amount of impurity as disclosed herein.

The following are non-limiting embodiments of disclosed compositions comprising 4-CBA:
a) terephthalic acid containing from about 0.01% to about 10% by weight 4-CBA; and
b) the balance one or more ionic liquids.

In another embodiment the impurities can be present in the impure terephthalic acid in an amount of from about 0.1% to about 7% by weight. In a further embodiment, the impurities can be present in an amount of from about 0.1% to about 5% by weight. In yet another embodiment, the impurities can be present in an amount of from 0.1% to about 4% by weight. A still further embodiment, the impurities can be present in an amount of from about 0.1% to about 3% by weight. However, one or more impurities may be present in an amount that is below the detection level by analytical methods, inter alia, GC/MS (gas chromatography in tandem with mass spectroscopy), nuclear magnetic resonance (NMR), and the like. The compositions of the present disclosure can encompass levels of impurities that are below the detection level by methods of analysis.

The disclosed compositions are provided by either:
 i) dissolving an aryl carboxylic acid in one or more ionic liquids to form a solution; or
 ii) dispersing an aryl carboxylic acid in one or more ionic liquids to form a dispersion.

A non-limiting example includes:
 i) dissolving terephthalic acid in one or more ionic liquids to form a solution; or
 ii) dispersing terephthalic acid in one or more ionic liquids to form a dispersion.

Processes

The processes of the present disclosure provide a low temperature, low water usage process for obtaining crystalline aryl carboxylic acids. In one aspect of the disclosed processes, the process is used to purify an aryl carboxylic acid. A major impurity resulting from one of the most common industrial processes for making terephthalic acid, is the partially oxidized benzoic acid derivative 4-carboxybenzaldehyde. Because terephthalic acid should be very pure to be used in processes for making polymers, for example, polyethyleneterephthalate resins, a large amount of the cost involved in terephthalic acid production goes toward the purification of this material.

A first aspect of the processes that encompass the present disclosure relates to processes for providing crystalline aryl carboxylic acids comprising:
- a) providing a composition comprising one or more aryl carboxylic acids and one or more ionic liquids; and
- b) combining the composition of step (a) with a non-solvent, thereby crystallizing the aryl carboxylic acid.

One iteration of this process relates to a process comprising:
- a) providing a composition comprising terephthalic acid and one or more ionic liquids; and
- b) combining the composition of step (a) with a non-solvent, thereby crystallizing terephthalic acid.

Step (a)

Step (a) encompasses providing a composition comprising an aryl carboxylic acid and one or more ionic liquids. The compositions of the disclosed processes are described herein above. The composition of this step may have one or more forms, for example, the disclosed compositions can be formed by either:
- i) dissolving one or more aryl carboxylic acids in one or more ionic liquids to form a solution; or
- ii) dispersing one or more aryl carboxylic acids in one or more ionic liquids to form a dispersion.

Therefore, in step (a) of the disclosed processes the composition can be in the form of a solution, a dispersion, or any other admixture form. The disclosure herein sets forth conditions and examples of the manner in which the compositions of the disclosed processes can be provided.

Step (b)

Step (b) of the disclosed process relates to addition of a non-solvent. The term "non-solvent" is defined herein as a molecular solvent for which the ionic liquid has high solubility and for which aryl carboxylic acid has little or no solubility. In addition, the non-solvent is chosen such that the impurities present in the processes for preparing crystalline aryl carboxylic acids, inter alia, terephthalic acid, have moderate to high solubility. An example of an impurity having higher solubility in a non-solvent is 4-carboxybenzaldehyde. The non-solvent can be a single molecular solvent, e.g., water, or a mixture of solvents, inter alia, methanol/water, ethanol/water. The relative compositions of solvent mixtures can be adjusted by the formulator depending upon the isolation conditions, for example, a single solvent can be used for the purification process disclosed herein, whereas a mixture of molecular solvents can be used when isolating the products of a reaction conducted in a composition comprising terephthalic acid and one or more ionic liquids.

Depending upon various factors, inter alia:
- i) the viscosity of the composition of step (a);
- ii) the temperature of the composition of step (a);
- iii) the amount of aryl carboxylic acid in the composition of step (a);
- iv) the presence of one or more impurities in the composition of step (a), the formulator can choose to either add the composition of step (a) to the non-solvent, or to add the non-solvent to the composition of step (a).

One non-limiting example of the processes disclosed herein involves the following: 100 mL of a 0.2 M composition of terephthalic acid and an ionic liquid (20 mmol of terephthalic acid in 100 mL of ionic liquid) at 70° C. is vigorously stirred. To this composition is added water (1000 mL). Crystalline terephthalic acid is obtained.

Lowering the viscosity of the composition provided in step (a) can aid the formulator in transferring the composition to a non-solvent or in adding a non-solvent to the composition of step (a).

Depending upon the concentration of the aryl carboxylic acid in the ionic liquid, the one or more impurities that can be present from the original synthesis of the aryl carboxylic acid, for example, terephthalic acid, can be more easily removed when the non-solvent is added in step (b). For example, the higher the solubility that the one or more impurities have in the non-solvent, the more concentrated the solution in step (a) can be.

If heating is desired, the heating can be conducted in manner that is suitable for use in processing the ionic liquid solutions, for example, steam heating via coils, heating via heating mantel, oil bath, steam bath, and the like.

The various aspects, embodiments, and iterations of the processes of present disclosure, as is further detailed herein, can further comprise the step:
- c) isolating a crystalline aryl carboxylic acid.

Isolation of the crystalline aryl carboxylic acid can be accomplished by any of the processes known to the artisan, inter alia, filtration, centrifugation, or extraction into a molecular solvent not miscible with the non-solvent or the ionic liquid.

The compositions of the present processes comprise an amount of aryl carboxylic acid and ionic liquids as described herein above.

The disclosed processes can also be used to purify aryl carboxylic acids. For example, a further embodiment of the disclosed processes relates to preparing crystalline aryl carboxylic acids wherein the aryl carboxylic comprises one or more impurities as described herein above. For example, a process comprising:
- a) providing a composition comprising terephthalic acid and one or more ionic liquids wherein the composition of step (a) comprises from about 0.001% to about 20% by weight of one or more impurities; and
- b) combining the composition of step (a) with a non-solvent, thereby crystallizing terephthalic acid.

Another example is a process comprising:
- a) providing a composition comprising terephthalic acid and one or more ionic liquids wherein the composition of step (a) comprises from about 0.01% to about 10% by weight of one or more impurities; and
- b) combining the composition of step (a) with a non-solvent, thereby crystallizing terephthalic acid.

In a further embodiment, the disclosed processes comprise:
- a) providing a composition comprising terephthalic acid and one or more ionic liquids wherein the composition of step (a) comprises from about 0.001% to about 20% by weight of 4-carboxyterephthalic acid; and
- b) combining the composition of step (a) with a non-solvent, thereby crystallizing terephthalic acid.

Removal of 4-carboxybenzaldehyde is important in the processes for preparing terephthalic acid. When present, the major process impurity 4-carboxybenzaldehyde not only gives the finished product a yellow cast, but only one moiety (carboxy group) of this molecule is capable of reaction with, for example, polyethylene glycols, under normal polymerization conditions to form an ester linkage. Reaction of this impurity during the polymerization process can result in chain termination, thereby causing the formulator to end up with a polymer having bulk properties not within the desired specifications.

The disclosed processes can reduce the amount of impurity in the crystalline aryl carboxylic acid by at least about 10% such that the amount of the one or more impurities present in the crystallize aryl carboxylic acid is 10% less than the amount present in the composition of step (a). As it relates to the purification of terephthalic acid, the disclosed processes can reduce the amount of impurity in the crystalline terephthalic acid by about 10% such that the amount of the one or more impurities present in the crystallize terephthalic acid is 10% less than the amount present in the composition of step (a).

In a further embodiment, the disclosed processes can reduce the amount of impurity in the crystalline terephthalic acid by about 25% such that the amount of the one or more impurities present in the crystallize terephthalic acid is about 25% less than the amount present in the composition of step (a).

In another embodiment, the disclosed processes can reduce the amount of impurity in the crystalline terephthalic acid by about 50% such that the amount of the one or more impurities present in the crystallize terephthalic acid is 50% less than the amount present in the composition of step (a).

In a yet further embodiment, the disclosed processes can reduce the amount of impurity in the crystalline terephthalic acid by about 75% such that the amount of the one or more impurities present in the crystallize terephthalic acid is 75% less than the amount present in the composition of step (a).

In a still further embodiment, the disclosed processes can reduce the amount of impurity in the crystalline terephthalic acid by about 90% such that the amount of the one or more impurities present in the crystallize terephthalic acid is 90% less than the amount present in the composition of step (a).

The disclosed processes can further comprise the step of isolating the crystalline aryl carboxylic acid, for example, a process for preparing a crystalline aryl carboxylic acid comprising:
a) providing a composition comprising an aryl carboxylic acids and one or more ionic liquids;
b) combining the composition of step (a) with a non-solvent, thereby crystallizing the aryl carboxylic acid; and
c) isolating the crystalline aryl carboxylic acid.

One iteration of this embodiment includes a process for preparing crystalline terephthalic acid comprising:
a) providing a composition comprising terephthalic acid and one or more ionic liquids;
b) combining the composition of step (a) with a non-solvent, thereby crystallizing the terephthalic acid; and
c) isolating the crystalline terephthalic acid.

A further iteration relates to compositions that comprise an impurity, the process for preparing crystalline terephthalic acid comprising
a) providing a composition comprising terephthalic acid and one or more ionic liquids wherein the composition of step (a) comprises from about 0.01% to about 20% by weight of one or more impurities;
b) combining the composition of step (a) with a non-solvent, thereby crystallizing terephthalic acid; and
c) isolating the crystalline terephthalic acid.

A non-limiting example of this iteration relates to a process for preparing crystalline terephthalic acid comprising:
a) providing a composition comprising terephthalic acid and one or more ionic liquids wherein the composition of step (a) comprises from about 0.01% to about 20% by weight of 4-carboxybenzaldehyde;
b) combining the composition of step (a) with a non-solvent, thereby crystallizing terephthalic acid; and
c) isolating the crystalline terephthalic acid.

Another aspect of the processes disclosed herein relate a to process comprising:
a) providing a composition comprising an aryl carboxylic acid and one or more ionic liquids; and
b) cooling the composition of step (a) and thereby crystallizing terephthalic acid.

One embodiment relates to a process for providing a crystalline aryl carboxylic acid comprising:
a) providing a composition comprising an aryl carboxylic acid and one or more ionic liquids at a first temperature; and
b) cooling the composition of step (a) to a second temperature and thereby crystallizing the aryl carboxylic acid.

One iteration of this process relates to a process for providing crystalline terephthalic acid comprising:
a) providing a composition comprising terephthalic and one or more ionic liquids at a first temperature; and
b) cooling the composition of step (a) to a second temperature and thereby crystallizing terephthalic acid.

A non-limiting example of a process for providing crystalline terephthalic acid wherein the terephthalic acid contains an impurity comprises:
a) providing a composition comprising terephthalic acid and one or more ionic liquids at a first temperature wherein the composition of step (a) comprises from about 0.001% to about 20% by weight of one or more impurities; and
b) cooling the composition of step (a) to a second temperature and thereby crystallizing terephthalic acid.

In addition, the processes of this aspect of the disclosure can further comprise a step for isolating the crystalline aryl carboxylic acid, for example, the process comprising:
a) providing a composition comprising terephthalic acid and one or more ionic liquids at a first temperature;
b) cooling the composition of step (a) to a second temperature and thereby crystallizing terephthalic acid; and
c) isolating the crystalline terephthalic acid.

Processes utilizing an isolation step can be applied equally well to processes of this aspect that comprise an aryl carboxylic acid containing an impurity, for example, the process for preparing crystalline terephthalic acid comprising:
a) providing a composition comprising terephthalic acid and one or more ionic liquids at a first temperature wherein the composition of step (a) comprises from about 0.001% to about 20% by weight of one or more impurities;
b) cooling the composition of step (a) to a second temperature and thereby crystallizing terephthalic acid; and
c) isolating the crystalline terephthalic acid.

Ionic liquids disclosed herein and further described herein below are a class of solvents composed of ionized species in contrast to traditional organic or aqueous solvents, which are molecular non-ionics. Ionic liquids are salts that exist in the liquid phase at a temperature from about −70° C. to about 300° C. In a first embodiment, of this aspect of the disclosed processes the composition in step (a) is provided at a temperature of from about 100° C. to about 200° C. In another embodiment, the composition in step (a) is provided at a temperature of from about 100° C. to about 150° C. In a further embodiment, the composition in step (a) is provided at a temperature of from about 100° C. to about 125° C. In a yet another embodiment, the composition in step (a) is provided at a temperature of from about 70° C. to about 150° C. In a still further embodiment, the composition in step (a) is provided at a temperature of from about 70° C. to about 100° C.

In a first embodiment of this aspect, of the disclosed processes the composition is cooled in step (b) to a temperature of from about 25° C. to about 150° C. In another embodiment, the composition is cooled in step (b) to a temperature of from about 25° C. to about 100° C. In a yet another embodiment, the composition is cooled in step (b) to a temperature of from about 25° C. to about 70° C. In further embodiment, the composition is cooled in step (b) to a temperature of from about 25° C. to about 50° C. In a yet further embodiment, the composition is cooled in step (b) to a temperature of from about 0° C. to about 50° C. In a still further embodiment, the composition is cooled in step (b) to a temperature of from about 15° C. to about 40° C.

In another embodiment of this aspect, the difference between the first temperature and the second temperature provides a means for preparing crystalline aryl carboxylic acids. In a first iteration the difference between the first temperature in step (a) and the second temperature in step (b) is from about 10° C. to about 100° C. In another iteration, the difference between the first temperature in step (a) and the second temperature in step (b) is from about 20° C. to about 90° C. In a yet another iteration the difference between the first temperature in step (a) and the second temperature in step (b) is from about 30° C. to about 80° C. In a still further iteration the difference between the first temperature in step (a) and the second temperature in step (b) is from about 10° C. to about 50° C. In a still yet further iteration the difference between the first temperature in step (a) and the second temperature in step (b) is from about 10° C. to about 25° C.

A non-limiting example of an iteration of this embodiment of this aspect of the disclosed processes relates to a process for providing crystalline terephthalic acid wherein the terephthalic acid contains one or more impurities, the process comprising:
  a) providing a composition comprising terephthalic acid and one or more ionic liquids at a first temperature of from about 100° C. to about 200° C. wherein the composition of step (a) comprises from about 0.001% to about 20% by weight of one or more impurities;
  b) cooling the composition of step (a) to a second temperature of from about 25° C. to about 70° C. and thereby crystallizing terephthalic acid; and
  c) isolating the crystalline terephthalic acid.

A further aspect of the disclosed processes relates to providing crystalline aryl carboxylic acids comprising:
  a) providing a composition comprising an aryl carboxylic acid and one or more ionic liquids; and
  b) combining the composition of step (a) with an immiscible liquid and thereby crystallizing the aryl carboxylic acid.

A non-limiting example of this aspect of the disclosed processes comprises;
  a) providing a composition comprising terephthalic acid and one or more ionic liquids; and
  b) combining the composition of step (a) with an immiscible liquid and thereby crystallizing terephthalic acid.

This aspect further comprises processes for preparing crystalline aryl carboxylic acids wherein the composition of step (a) contains one or more impurities as described herein above. For example a process for preparing crystalline terephthalic acid comprising:
  a) providing a composition comprising terephthalic acid and one or more ionic liquids wherein the composition of step (a) comprises from about 0.001% to about 20% by weight of one or more impurities; and
  b) combining the composition of step (a) with an immiscible liquid and thereby crystallizing terephthalic acid.

In addition, the disclosed processes can further comprise the step of isolating the crystallize aryl carboxylic acid, for example, crystallized terephthalic acid.

The immiscible liquids of the disclosed processes are any organic liquid or solvent that is immiscible in the one or more ionic liquids of step (a) and in which the aryl carboxylic acid is also insoluble. Non-limiting examples of immiscible liquids that can be used for step (b) include alkane solvents, inter alia, pentane, iso-pentane, hexane, heptane, octane, isooctane, and the like; aromatic hydrocarbon solvents, inter alia, benzene, toluene, and xylene (all isomers); ethers, inter alia, diethyl ether, tetrahydrofuran, and dioxane; and various fluorinated and chlorinated hydrocarbons; esters, inter alia, ethyl acetate, methyl acetate, and the like; ketones, inter alia, acetone, 2-butanone, and the like. In addition, mixtures of one or more of these solvents can be used as the immiscible liquid.

The processes disclosed herein make use of the unique properties of ionic liquids to solve the problem of lowering the cost and efficiency of purifying aryl carboxylic acids, for example, terephthalic acid. Terephthalic acid is insoluble in water at temperatures below about 200° C. and the solubility only increases substantially at temperatures above about 250° C. 4-Carboxybenzaldehyde is soluble in water. Ionic liquids are typically soluble in water and other polar solvents.

Ionic liquids are a class of solvents composed of ionized species in contrast to traditional organic or aqueous solvents which are molecular non-ionics. Ionic liquids are salts that exist in the liquid phase at a temperature from about −70° C. to about 300° C. The ionic liquids of the present disclosure comprise an organic cation and an organic or inorganic anion. The organic cation is typically formed by alkylation of a neutral organic species capable of holding a positive charge when a suitable anion is present.

The organic cation of the ionic liquids disclosed herein can comprise a linear, branched, or cyclic heteroalkyl unit. The term "heteroalkyl" refers to a cation as disclosed herein comprising one or more heteroatoms chosen from nitrogen, oxygen, sulfur, boron, or phosphorous capable of forming a cation. The heteroatom can be a part of a ring formed with one or more other heteroatoms, for example, pyridinyl, imidazolinyl rings, that can have substituted or unsubstituted linear or branched alkyl units attached thereto. In addition, the cation can be a single heteroatom wherein a sufficient number of substituted or unsubstituted linear or branched alkyl units are attached to the heteroatom such that a cation is formed. For example, the ionic liquid tributylmethyl phosphonium dimethyl-phosphate having the formula:

is an example of an ionic liquid wherein the heteroalkyl cation comprising linear alkyl units; three n-butyl ($C_4$) units and one methyl ($C_1$) unit. N-Ethyl-3-methyl-pyridinium ethylsulfate having the formula:

is an example of an ionic liquid comprising a cyclic heteroalkyl cation; a ring comprising 5 carbon atoms and 1 nitrogen atom. When more than one quaternizable heteroatom is present in a ring, only one heteroatom is alkylated.

Non-limiting examples of heterocyclic and heteroaryl units that can be alkylated to form cationic units include imidazole, pyrazoles, thiazoles, isothiazoles, azathiozoles, oxothiazoles, oxazines, oxazolines, oxazaboroles, dithiozoles, triazoles, selenozoles, oxahospholes, pyrroles, boroles, furans, thiphenes, phospholes, pentazoles, indoles, indolines, oxazoles, isothirazoles, tetrazoles, benzofuran, dibenzofurans, benzothiophenes, dibenzothoiphenes, thiadiazoles, pyrdines, pyrimidines, pyrazines, pyridazines, piperazines, piperidines, morpholines, pyrans, annolines, phthalazines, quinazolines, and quinoxalines.

The following are examples of heterocyclic units that are suitable for forming a cyclic heteroalkyl cation unit of the disclosed ionic liquids:

pyrrolidinium     piperidinium

The following are further examples of heterocyclic units that are suitable for forming a cyclic heteroalkyl cation unit of the disclosed ionic liquids:

pyridinium     pyridazinium pyrimidinium     pyrazinium imidazolium     pyrazolium oxazolium 1,2,3-triazolium 1,2,4-triazolium     thiazolium quinolium isoquinolium where each $R^1$ and $R^2$ is, independently, a substituted or unsubstituted linear, branched, or cyclic $C_1$-$C_6$ alkyl, or substituted or unsubstituted linear, branched, or cyclic $C_1$-$C_6$ alkoxy; each $R^3$, $R^4$, $R^5$, $R^6$, $R^7$, $R^8$, and $R^9$ is, independently, hydrogen, substituted or unsubstituted linear, branched, or cyclic $C_1$-$C_6$ alkyl, substituted or unsubstituted linear, branched, or cyclic $C_1$-$C_6$ alkoxy, or substituted or unsubstituted linear or branched, $C_1$-$C_6$ alkoxyalkyl.

The following comprises yet another set of examples of heterocyclic units that are suitable for forming heterocyclic dication units of the disclosed ionic liquids and are referred to as such or as "geminal ionic liquids:" See Armstrong, D. W. et al., Structure and properties of high stability geminal dicationic ionic liquids, *J. Amer. Chem. Soc.* 2005; 127(2):593-604; and Rogers, R. D. et al., Mercury(II) partitioning from aqueous solutions with a new, hydrophobic ethylene-glycol functionalized bis-imidazolium ionic liquid, *Green Chem.* 2003; 5:129-135 included herein by reference in its entirety.

1,1'-[1,2-ethanediylbis(oxy-1,2-ethanediyl)]bis[3-methyl-1H-imidazolium-1-yl]

n= 3, 6, 9, 12        n= 3, 9

Imidazolium and Pyrrolidinium Based Di-Cations where $R^1$, $R^4$, $R^9$, and $R^{10}$ comprise a substituted or unsubstituted linear, branched, or cyclic $C_1$-$C_6$ alkyl, or substituted or unsubstituted linear, branched, or cyclic $C_1$-$C_6$ alkoxy; each $R^5$, $R^6$, $R^7$, and $R^8$ is, independently, hydrogen, substituted or unsubstituted linear, branched, or cyclic $C_1$-$C_6$ alkyl, substituted or unsubstituted linear, branched, or cyclic $C_1$-$C_6$ alkoxy, or substituted or unsubstituted linear or branched, $C_1$-$C_6$ alkoxyalkyl.

The anionic portion of the ionic liquid can comprise an inorganic or organic moiety. Non-limiting examples of anions include inorganic anions: halogens, (i.e., F, Cl, Br, and I); borides, $BX_4$, wherein X represents halogen, (i.e., $BF_4$, $BCl_4$), and the like; phosphates(V), $PX_6$; $PF_6$, and the like; arsenate(V), $AsX_6$; $AsF_6$, and the like; stibate(V) (antimony), $SbX_6$; $SbF_6$, and the like; $CO_3^{2-}$; $NO_2$, $NO_3$, $SO_4^{2-}$, and $(CF_3)SO_3$.

Other non-limiting examples of ionic liquid anions include substituted azolates, that is, five membered heterocyclic aromatic rings that have nitrogen atoms in either positions 1 and 3 (imidazolates); 1, 2, and 3 (1,2,3-triazolates); or 1, 2, 4 (1,2,4-triazolate). Substitutions to the ring occur at positions that are not located in nitrogen positions (these are carbon positions) and include CN (cyano-), $NO_2$ (nitro-), and $NH_2$ (amino) group appended to the heterocyclic azolate core.

Further non-limiting examples of anions include substituted or unsubstituted borides: $B(R^{10})_4$; substituted or unsubstituted sulfates: $(R^{10}O)S(=O)_2O$; substituted or unsubstituted acyl units $R^{10}CO_2$, for example, acetate $CH_3CO_2$, proprionate, $CH_3CH_2CO_2$, butyrate $CH_3CH_2CH_2CO_2$, and benzylate, $C_6H_5CO_2$; substituted or unsubstituted phosphates: $(R^{10}O)_2P(=O)O$; substituted or unsubstituted carboxylates: $(R^{10}O)C(=O)O$; substituted or unsubstituted azolates wherein the azolate can be substituted on a carbon atom by a unit chosen from cyano, nitro, and amino. Non-limiting examples of $R^{10}$ include hydrogen; substituted or unsubstituted linear branched, and cyclic alkyl; substituted or unsubstituted linear, branched, and cyclic alkoxy; substituted or unsubstituted aryl; substituted or unsubstituted aryloxy; substituted or unsubstituted heterocyclic; substituted or unsubstituted heteroaryl; acyl; silyl; boryl; phosphino; amino; thio; and seleno.

One embodiment of ionic liquids comprise an anion chosen from Cl, Br, I, $(CF_3)SO_3$, $(R^{10}O)S(=O)_2O$; $(R^{10}O)_2P(=O)O$; $(R^{10}O)C(=O)O$; and $R^{10}CO_2$; each $R^{10}$ is independently $C_1$-$C_4$ alkyl. Anions that are chosen from Cl, Br, I, and $R^{10}O_2$ have been found to be convenient in forming the compositions of step (a) in the compositions and processes disclosed herein.

The following is a description of the short hand method used throughout the specification for referring to the imidazolium-based ionic liquids disclosed herein. The template:

[$C_n$mim]

represents the cation portion of the ionic liquid wherein $C_n$ represent an alkyl or substituted alkyl moiety having n number of carbon atoms. The term "mim" refers to "methyl substituted imidazolium." Referring to the generic imidazolium formula:

wherein $R^3$, $R^4$, and $R^5$ are each hydrogen, can also be written as follows:

wherein either nitrogen can be depicted as having a positive charge. By the convention used herein the methyl group of "mim" refers to the $R^1$ moiety and the $C_n$ substituent is the $R^2$ moiety. Therefore [$C_4$mim] represents a cation having the formula:

which can be equally well represented by the formula:

The anion portion of the ionic liquid is written without the charge, for example, Cl and $PF_6$.

The following are non-limiting examples or ionic liquids written in the short hand convention with the corresponding formula:

i) [C₄mim]Cl having the formula:

ii) [C₂mim](C₂H₅O)SO₃ having the formula:

iii) [C₄mim]Cl having the formula:

iv) [C₂mim]Cl having the formula:

v) [C₂ mim](C₂H₅O)₂PO₂ having the formula:

vi) [C₄mim]BF₄ having the formula:

and vii) [C₄mim]PF₆ having the formula:

Because ionic liquids have a solvent behavior different than traditional molecular solvents, e.g., water, traditional organic, and organic/aqueous combinations, compositions comprising one or more ionic liquids can allow the formulator to perform chemical reactions under conditions and with results not obtainable with traditional molecular solvents.

For example, reactions that typically are conducted at elevated temperatures can be conducted at temperatures at or near room temperature because of the high solubility of many organic molecules, oligomers, or other substrates in ionic liquids.

Because it has now been found that molecular species such as terephthalic acid are soluble in various ionic liquids at temperatures as low as 70° C., compositions comprising terephthalic acid can be utilized for derivatization of terephthalic acid, as well as for conducting polymerization reactions or for making other derivatives of terephthalic acid. Therefore, the processes disclosed herein can further encompass one or more steps wherein a chemical reaction is involved.

A first embodiment of this aspect of the disclosed processes relates to chemical reaction which utilize the compositions disclosed herein to react an aryl carboxylic acid with a chemical reagent. For example, a composition comprising terephthalic acid and one or more ionic liquids can be used to react the terephthalic acid with ethylene glycol to form a pre-polymer, polymer, or with a polyalkylene glycol to form a block co-polymer.

This embodiment of the disclosed processes comprises:
a) providing a composition comprising terephthalic acid and one or more ionic liquids; and
b) combining the composition of step (a) with one or more chemical reagents and thereby forming a reaction product resulting from the one or more chemical reagents chemically reacting with the terephthalic acid.

The following is a non-limiting example of a reaction which terephthalic acid can undergo in a composition as disclosed herein:

wherein n is an integer from 1 to 100.

The following is a non-limiting example of the compositions disclosed herein being used for reacting terephthalic acid.

Purified terephthalic acid (16.6 g, 100 mmol) comprising less than 0.1% by weight of a material other than terephthalic acid is dissolved or dispersed in [C₄mim]Cl (1 L) and stirred. Ethylene glycol having the molecular formula HOCH₂CH₂OH (6.21 g, 100 mmol) is added and the temperature slowly raised to about 100° C. After allowing the reaction to proceed, the solution is cooled to about 50° C. and water is added (5 L). After allowing the admixture to cool to room temperature methylene chloride (100 mL) is added and the organic layer removed, washed twice with water (50 mL) and the solvent is removed in vacuo to afford the block copolymer of terephthalic acid and ethylene glycol.

The disclosed processes can comprise one or more chemical reagents chosen from:
i) aliphatic or aromatic alcohols;
ii) polyalkylene glycols; and
iii) amines or polyamines.

The disclosed processes can comprise a catalyst for use with hydrogen gas (reduction reactions, removal of protecting groups) or oxygen gas (oxidation reactions, and the like).

In addition, the processes disclosed herein can be used with a reducing reagent or an oxidizing reagent, for example, $NaBH_4$, $LiBH_4$, Al(iso-propoxy)$_3$, and the like.

This embodiment of the disclosed processes can further comprise an isolation step as described herein above.

Another embodiment of this aspect of the disclosed processes relates to processes wherein one or more impurity is present in the composition of step (a) and a reagent is added to further react the one or more impurities in a manner that converts the one or more impurity to an aryl carboxylic acid or to a form that is more easily removed when step (b) of the disclosed processes is performed.

The non-limiting examples of further iterations of this embodiment are exemplified using terephthalic acid as the aryl carboxylic acid. For example, a process for preparing crystalline terephthalic acid comprising
- a) providing a composition comprising terephthalic acid containing one or more impurities and one or more ionic liquids, wherein at least one of the impurities is 4-carboxybenzaldehyde;
- b) combining a reagent capable of further oxidizing 4-carboxybenzaldehyde to terephthalic acid;
- c) oxidizing 4-carboxybenzaldehyde to terephthalic acid; and
- d) combining the composition of step (c) with a non-solvent, thereby crystallizing terephthalic acid.

This aspect of the process disclosed herein can also further comprise:
- e) isolating the crystalline terephthalic acid.

The reagent capable of oxidizing the remaining 4-carboxybenzaldehyde can be any reagent chosen by the formulator that is compatible with the objectives of the other steps. For example, the reagent cannot react further with terephthalic acid or any of the ionic liquids present. In addition, the reagent should be compatible with the non-solvents, for example, non-reactive. However, the non-solvent can be used to also quench the oxidation reaction.

In an iteration of this embodiment, steps (b) and (c) can comprise:
- b) combining a reagent capable of converting residual 4-carboxybenzaldehyde or other impurities into a compound that is more soluble in the non-solvent than in the one or more ionic liquids;
- c) converting 4-carboxybenzaldehyde or other impurities into a compound that is more soluble in the non-solvent than in the one or more ionic liquids.

For the purposes of the present disclosure, a "compound that is more soluble in the non-solvent than in the one or more ionic liquids" is defined as a compound having a solubility in the non-solvent of at least two times the solubility of the compound in the one or more ionic liquids.

In a further embodiment of the present disclosure relates to a two stage process for providing crystalline terephthalic acid comprising:
- a) providing a composition comprising terephthalic acid containing two or more impurities in one or more ionic liquids, wherein one of the impurities is 4-carboxybenzaldehyde and one of the impurities is not 4-carboxybenzaldehyde;
- b) combining a reagent capable of further oxidizing 4-carboxybenzaldehyde to terephthalic acid;
- c) oxidizing 4-carboxybenzaldehyde to terephthalic acid to form a reaction admixture comprising oxidized 4-carboxybenzaldehyde and the one or more other impurities from step (a) that are not 4-carboxybenzaldehyde;
- d) combining the reaction solution formed in step (c) with a non-solvent thereby crystallizing terephthalic acid;
- e) separating the crystalline terephthalic acid from the non-solvent wherein the impurity from step (a) that is not 4-carboxybenzaldehyde is still present;
- f) providing a composition comprising the crystalline terephthalic acid from step (e) and one or more ionic liquids used in step (a); and
- g) combining the composition of step (f) with a non-solvent, thereby crystallizing terephthalic acid.

An additional step can be added to this iteration that includes the step of:
- h) isolating crystalline terephthalic acid.

It can be advantageous for the formulator to use this latter iteration of the present process when high amounts of impurities are present in the crude terephthalic acid and the distribution co-efficient of the impurity that is not 4-carboxybenzaldehyde is such that this second impurity is much less soluble in the non-solvent and therefore a re-processing sequence can be advantageous to the formulator.

Procedures

Examples illustrating the dissolution and aqueous reconstitution of terephthalic acid from ionic liquids follow the same general experimental protocol. However, it should be noted that the ionic liquids chosen are by far non-limiting examples of terephthalic acid dissolution in ionic liquids. To a vial containing 100 mg of an ionic liquid is added 10 mg of terephthalic acid and the mixture is heated to 75° C. to reduce the viscosity of the resulting liquid. The solution is stirred on a hot plate in an oil bath for 24 hours, whereupon the solutions are visually checked for dissolution. Aqueous reconstitution of the terephthalic acid is achieved by the addition of 500 mL deionized water (polished to 18.1-18.3 MΩ cm). Crystalline terephthalic acid separates from the ionic liquid as a flock, washed with copious amounts of deionized water and vacuum filtered, then dried in ambient conditions and ground with a spatula to give the desired crystalline terephthalic acid.

Figure 1:
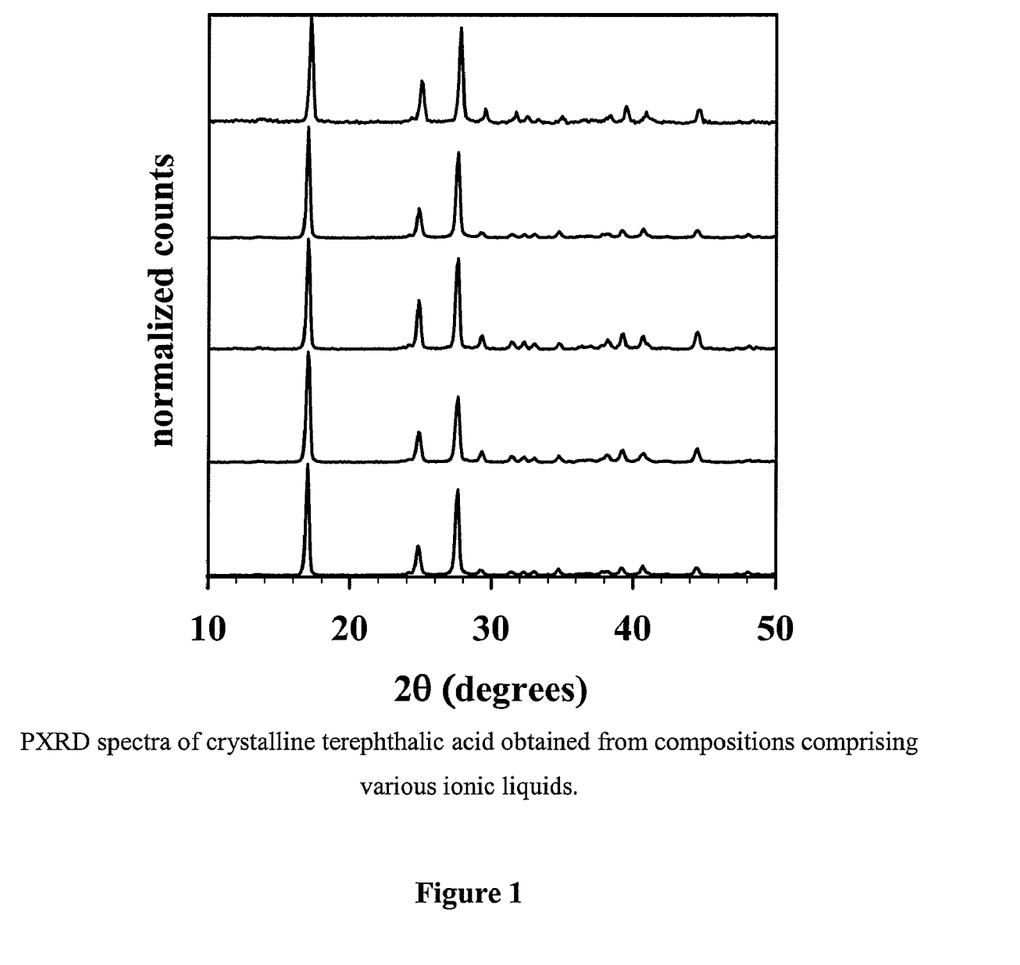
FIG. 1 depicts the X-ray powder diffraction spectra for 4 samples of crystalline terephthalic acid obtained from compositions comprising various ionic liquids. From top to bottom the ionic liquids are: [$C_2$mpy][EtSO$_4$], [$C_2$mim][EtSO$_4$], [$C_2$mim]Cl, and [$C_4$ mim]Cl.

FIG. 1 shows the powder X-ray diffraction spectra that were taken for crystalline terephthalic acid obtained from compositions comprising different ionic liquids to determine the composition of the terephthalic acid flock. The top spectrum was obtained on crystalline terephthalic acid wherein the composition comprised [$C_2$ mpy][$EtSO_4$] as the ionic liquid. The next spectrum was obtained on crystalline terephthalic acid wherein the composition comprised [$C_4$mim][$EtSO_4$] as the ionic liquid. The third spectrum from the top was obtained on crystalline terephthalic acid wherein the composition comprised [$C_2$mim]Cl as the ionic liquid. The bottom spectrum was obtained on crystalline terephthalic acid wherein the composition comprised [$C_4$mim]Cl as the ionic liquid.

Data were collected on a Rigaku Geigerflex D/Max-2BX Horizontal XRD Thin Film Diffractometer equipped graphite monochromated with an Ni filter Cu/Kα radiation (long focus used in line-focus mode 1.5418 Å), passing through a ½° divergence slit, 0.40 mm scatter slit, and 0.40 mm scatter slit before counting with a CCD area detector. A radius arm of 185 mm was employed for continuous detection from θ=10-50° with a step of 0.1° at a rate of 1.2° min$^{-1}$.

Purification of terephthalic acid containing 4-carboxybenzaldehyde as an impurity was achieved, resulting in a 23.8% reduction in 4-carboxybenzaldehyde after processing with an ionic liquid at 75° C. Detection of both terephthalic acid and 4-carboxybenzaldehyde content was carried out with IC using the procedure disclosed herein. In general, in order to ionize the aryl carboxylic acid to be detected by ion chromatography, a 0.1 M solution of KOH was used to dissolve and dilute all standard and unknown samples. Stock solutions containing 100 ppm TPA and 4-CBA were made by dissolving the appropriate amount of aryl carboxylic acid into a 100 mL volumetric flask. All subsequent standards were made by serial dilution from this standard.

All chromatographic data were collected on a Dionex™ (Sunnyvale, Calif.) DX 500 Chromatography Systems equipped with an IP25 isocratic pump and an AD20 absorbance detector set at a collection wavelength of 254 nm. The column (Dionex IonPac® AS11-HC, Analytical 2×250 mm) and guard column (Dionex IonPac® AG11-HC, Analytical 2×50 mm) were eluted at 0.50 mL min$^{-1}$ with helium degassed 0.1 M KOH delivered from an eluent reservoir organizer. Sample injection was pneumatic with a 25 µL injection loop, and data runs were carried out to 20 minutes to allow the column to equilibrate between each run. Peak analyses were carried out on the spectra with SSPS PeakFit® software (Chicago, Ill.).

In one example, terephthalic acid containing an impurity (0.3021 g, 1.818 mmol: assuming 100% terephthalic acid for the sake of calculation) obtained from the oxidation of para-xylene was weighted and added to [C$_4$mim]Cl (6.0172 g, 34.45 mmol) at room temperature. The solution was then raised to 75° C. in order to lower the viscosity of the resulting liquid. In one embodiment, 6.0172 g of a 0.3021 M solution of terephthalic aid in an ionic liquid (302.1 mmol of terephthalic acid in 6.0172 g of ionic liquid) at 75° C. was vigorously stirred. To this solution was added water (500 mL). Crystalline terephthalic acid was obtained and the amount of 4-carboxybenzaldehyde present in the original composition is then determined.

Figure 2:
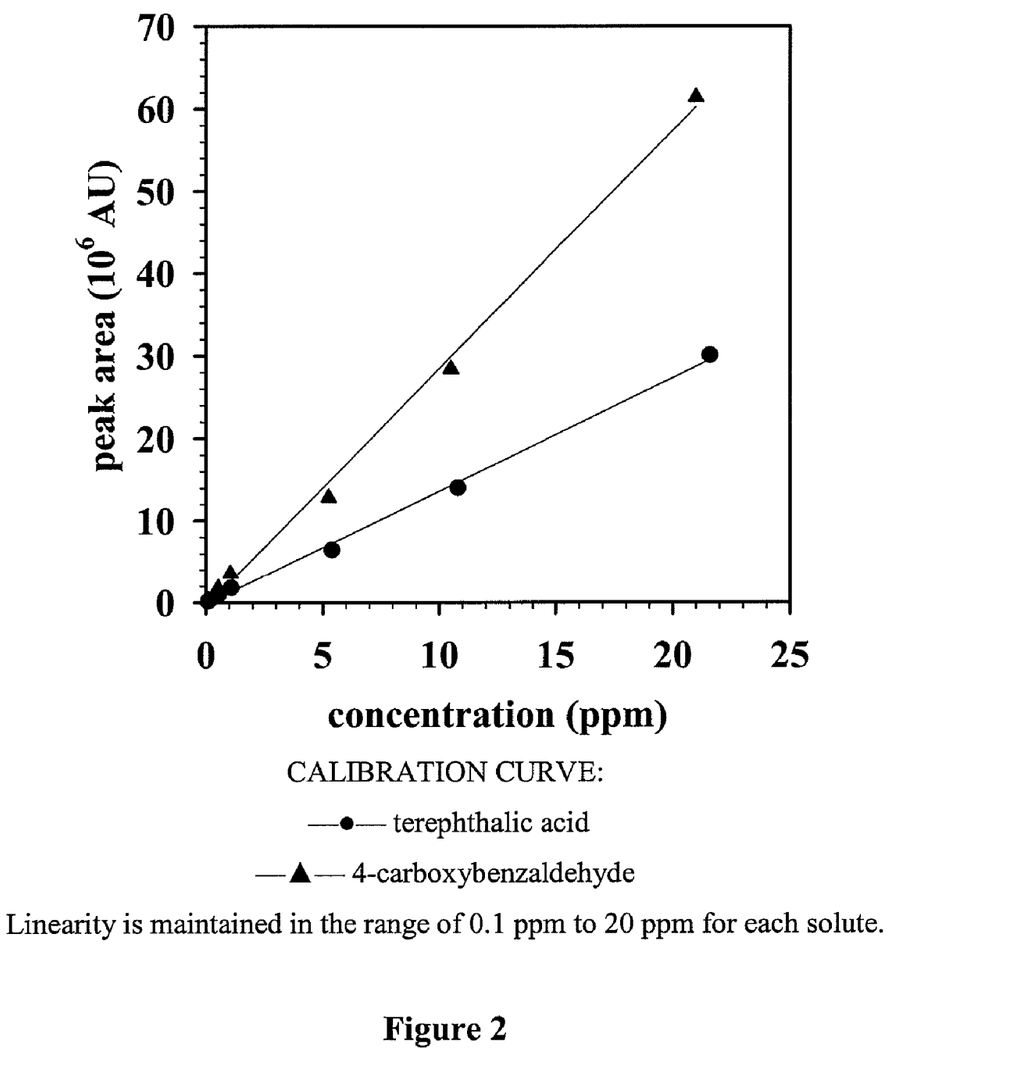
FIG. 2 depicts the standard calibration curve for compositions comprising terephthalic acid and 4-carboxybenzaldehyde as an impurity obtained using a DIONEX™ DX 500 Ion Chromatography System.

FIG. 2 show the standard calibration curve for compositions comprising terephthalic acid and 4-carboxybenzaldehyde as an impurity. The amount of 4-carboxybenzaldehyde found in the original sample was by weight 0.21%. This amount was reduced to 0.16% after processing with [C$_4$mim] Cl at 75° C., for a reduction in 4-carboxybenzaldehyde of 23.8%.

The present disclosure further relates to salts of aryl carboxylic acids wherein the aryl carboxylic acid is the anion and the cation is an organic moiety. In one embodiment the cation is also a cation as disclosed herein as a cation that forms an ionic liquid.

The following is a non-limiting example of the preparation of a salt of terephthalic acid according to the present disclosure. Synthesis of the 1,3-dimethylimidazolim salt, [1,3-dimim-2-COO$^-$], of terephthalic acid was carried out using previously described methods (See Rogers, R. D., et al., 1,3-Dimethylimidazolium-2-carboxylate: the unexpected synthesis of an ionic liquid precursor and carbene-CO2 adduct, *Chem. Commun.*; 2003: 28-29).

Figure 3:
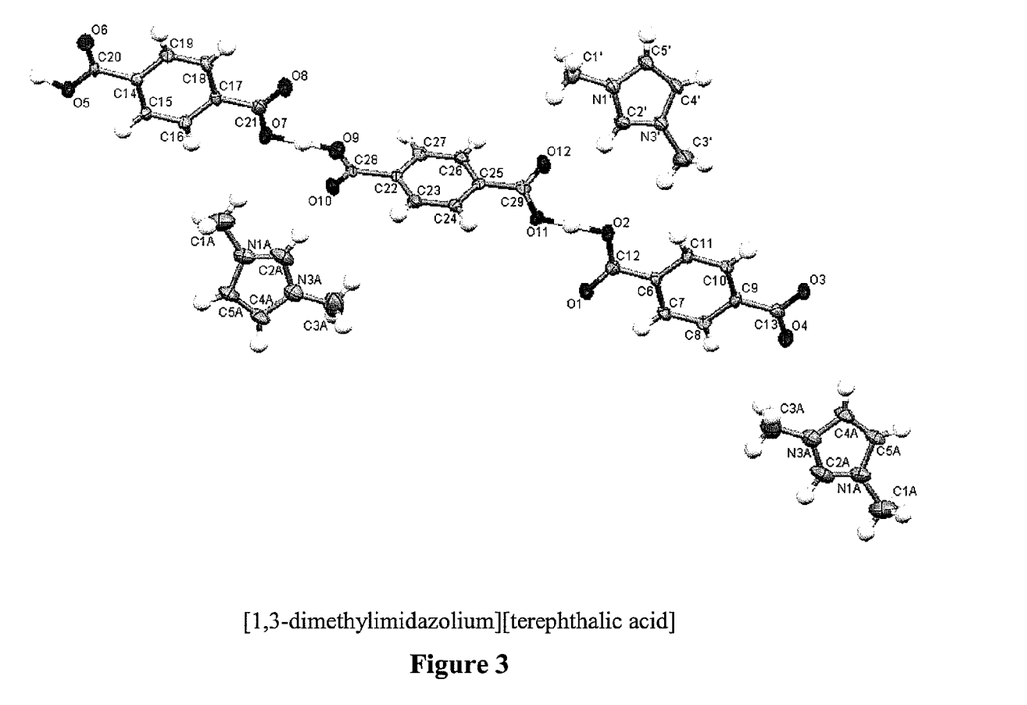
FIG. 3 depicts the ORTEP III plot of [1,3-dimethylimidazolium][terephthalic acid].

The formulator can determine the ratio of cations to aryl carboxylate anion by the choice of conditions when forming the salts disclosed herein. For example, the mono-1,3-dimethylimidazolium salt of terephthalic acid can be formed according to the scheme:

as follows. In a round bottom flask is added 1 mol of terephthalic acid and 2.1 mol of [1,3-dimim-2-COO$^-$] and 5 mL of DMSO. The mixture is stirred at 60° C. for 24 hours after which water is added. Crystallization of this solution affords the mono-cation salt.

Figure 4:
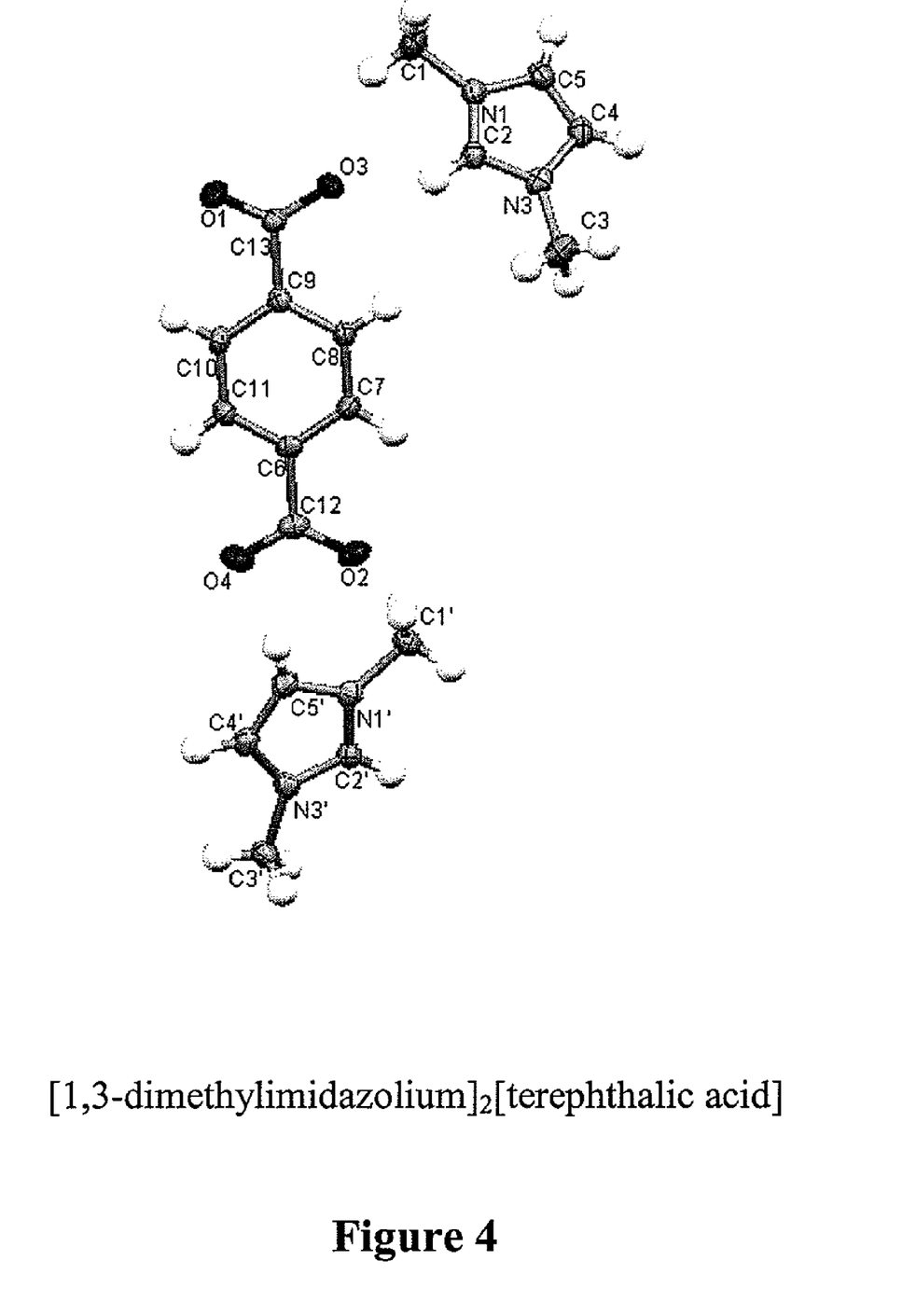
FIG. 4 depicts the ORTEP III plot of [1,3-dimethylimidazolium]$_2$[terephthalic acid].
Figure 5:
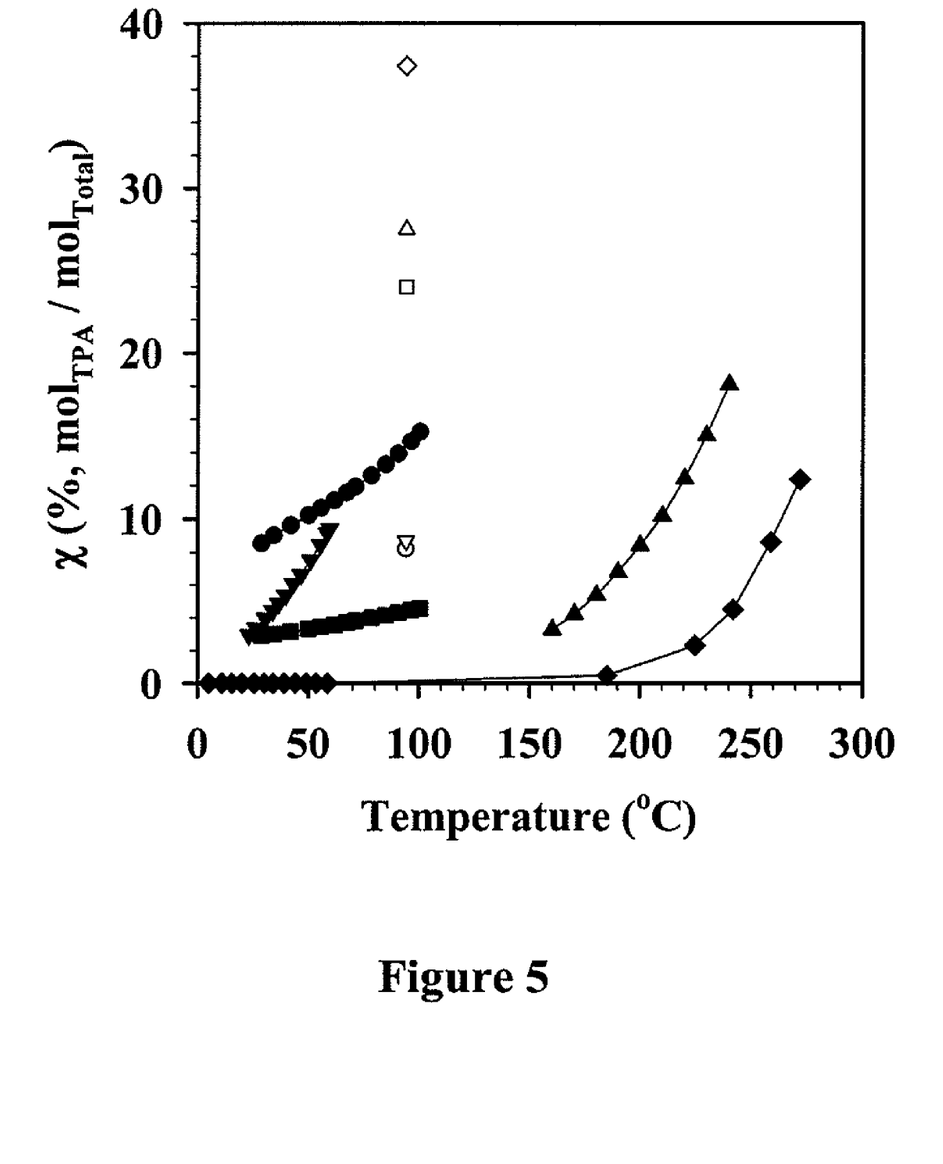
FIG. 5 is a graph of solubility data in percent mole fraction of TPA in ILs compared with conventional solvents: (◇) [$C_2$mim][Et$_2$PO$_4$], (△) [$C_4$mim]Cl, (□) [$C_2$mim]Cl, (▽) [$C_2$mpy][EtSO$_4$], and (○) [$C_2$mim][EtSO$_4$]. Conventional solvents shown are: (•) water, (▲) HOAc, (■) DMF, (▼) N-methyl-pyrrolidone, and (●) DMSO.

However, crystallization without the addition of water affords the di-cation salt according to the following scheme:

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for providing crystalline terephthalic acid comprising:
    a) providing a composition comprising 5% to 99% by weight of terephthalic acid and one or more ionic liquids, wherein the ionic liquids comprise:
        a) a cation formed from an alkylated heterocyclic or heteroaryl unit chosen from imidazole, pyrazole, thiazole, isothiazole, azathiozole, oxothiazole, oxazine, oxazoline, oxazaborole, dithiozole, triazole, selenozole, oxahosphole, pyrrole, borole, furan, thiophene, phosphole, pentazole, indole, indoline, oxazole, isothirazole, tetrazole, benzofuran, dibenzofuran, benzothiophene, dibenzothoiphene, thiadiazole, pyrdine, pyrimidine, pyrazine, pyridazine, piperazine, piperidine, morpholine, pyran, annoline, phthalazine, quinazoline, and quinoxaline; and b) an anion chosen from:
   i) $F^-$, $Cl^-$, $Br^-$, and $I^-$;
   ii) $BX_4^-$; $PX_6^-$; $AsX_6^-$; and $SbX_6^-$; wherein $X^-$ is a halogen chosen from $F^-$, $Cl^-$, $Br^-$, and $I^-$;
   iii) $NO_2^-$;
   iv) $NO_3^-$;
   v) $SO_4^{2-}$;
   vi) $(CF_3)SO_3^-$;
   vii) substituted or unsubstituted) $B(R^{10})_4^-$;
   viii) substituted or unsubstituted $(R^{10}O)S(=O)_2O^-$;
   ix) substituted or unsubstituted $(R^{10}O)_2PO^-$;
   x) substituted or unsubstituted $R^{10}CO_2^-$;
   xi) substituted or unsubstituted $(R^{10}O)_2P(=O)O^-$;
   xii) substituted or unsubstituted $(R^{10}O)C(=O)O^-$;
   xiii) substituted of unsubstituted azolate;
   $R^{10}$ is independently hydrogen; substituted or unsubstituted linear; branched, and cyclic alkyl; substituted or unsubstituted linear, branched, and cyclic alkoxy; substituted or unsubstituted aryl; substituted or unsubstituted aryloxy; substituted or unsubstituted heterocyclic; substituted or unsubstituted heteroaryl; acyl; silyl; boryl; phosphino; amino; thio; and seleno; or wherein the azolate can be substituted on a carbon atom by a unit chosen from cyano, nitro, and amino; and
b) combining the composition of step (a) with a non-solvent, thereby crystallizing terephthalic acid.

2. The process according to claim 1, wherein the ionic liquid is chosen from

3. The process according to claim 1, wherein the non-solvent is water.

4. The process according to claim 1, further comprising:
   c) isolating the crystalline terephthalic acid.

5. A process for providing crystalline terephthalic acid comprising:
   a) providing a composition comprising 5% to 99% by weight of terephthalic acid and one or more ionic liquids; and
   b) combining the composition of step (a) with an immiscible liquid and thereby crystallizing terephthalic acid wherein the immiscible liquid is selected from alkane solvents, aromatic hydrocarbon solvents, ethers, fluorinated and chlorinated hydrocarbons, esters and ketones.

6. A process for preparing crystalline terephthalic acid comprising
   a) providing a composition comprising 5% to 99% by weight of terephthalic acid containing one or more impurities and one or more ionic liquids, wherein at least one of the impurities is 4-carboxybenzaldehyde;
   b) combining a reagent capable of further oxidizing 4-carboxybenzaldehyde to terephthalic acid;
   c) oxidizing 4-carboxybenzaldehyde to terephthalic acid; and
   d) combining the composition of step (c) with a non-solvent, thereby crystallizing terephthalic acid.

* * * * *